(12) United States Patent
Thomas et al.

(10) Patent No.: US 12,285,176 B2
(45) Date of Patent: Apr. 29, 2025

(54) MULTI-PIECE LIGATION CLIP

(71) Applicant: Covidien LP, Mansfield, MA (US)

(72) Inventors: Justin Thomas, New Haven, CT (US); Roy J. Pilletere, Middletown, CT (US); Matthew A. Dinino, Newington, CT (US); Gregory R. Morck, Haddam, CT (US); Saumya Banerjee, Southington, CT (US); Eric Brown, Madison, CT (US); Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/214,761

(22) Filed: Jun. 27, 2023

(65) Prior Publication Data

US 2023/0338039 A1 Oct. 26, 2023

Related U.S. Application Data

(62) Division of application No. 16/866,649, filed on May 5, 2020, now Pat. No. 11,707,282.

(60) Provisional application No. 62/869,584, filed on Jul. 2, 2019.

(51) Int. Cl.
*A61B 17/122* (2006.01)
*A61B 17/128* (2006.01)

(52) U.S. Cl.
CPC .......... *A61B 17/122* (2013.01); *A61B 17/128* (2013.01)

(58) Field of Classification Search
CPC ... A61B 17/122; A61B 17/1227; A61B 17/08; A61B 17/083; A61B 2017/1225; A61B 2017/081
See application file for complete search history.

(56) References Cited

U.S. PATENT DOCUMENTS

| | | |
|---|---|---|
| 3,040,749 A | 6/1962 | Payton |
| 3,439,523 A | 4/1969 | Wood |
| 3,713,533 A | 1/1973 | Reimels |
| 4,076,120 A | 2/1978 | Carroll et al. |
| 4,146,130 A | 3/1979 | Samuels et al. |
| 4,187,712 A | 2/1980 | Samuels et al. |
| 4,212,303 A | 7/1980 | Nolan |
| 4,212,390 A | 7/1980 | Raczkowski et al. |
| 4,294,355 A | 10/1981 | Jewusiak et al. |
| 4,344,531 A | 8/1982 | Giersch |

(Continued)

FOREIGN PATENT DOCUMENTS

| | | |
|---|---|---|
| BE | 654195 A | 2/1965 |
| CN | 204839635 U | 12/2015 |

(Continued)

OTHER PUBLICATIONS

Chinese International PCT Application No. PCT/CN2018/078294 filed Mar. 7, 2018, Covidien LP.

(Continued)

*Primary Examiner* — Katherine H Schwiker
(74) *Attorney, Agent, or Firm* — Draft Masters IP, LLC

(57) ABSTRACT

Polymeric ligation clips and a clip applier for applying a polymeric ligation clip to tissue are disclosed herein. More particularly, the polymeric ligation clips include separate first and second beams that can be coupled to each other and are movable from a reduced diameter open position in which minimal strain is placed on the ligation clip to a clamped position and to a clip applier for delivering such a ligation clip to a surgical site.

12 Claims, 15 Drawing Sheets

(56) References Cited

U.S. PATENT DOCUMENTS

| | | |
|---|---|---|
| 4,346,869 A | 8/1982 | MacNeill |
| 4,361,229 A | 11/1982 | Mericle |
| 4,390,019 A | 6/1983 | LeVeen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |
| 4,487,205 A | 12/1984 | Di Giovanni et al. |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,942,886 A | 7/1990 | Timmons |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,411,481 A | 5/1995 | Allen et al. |
| 5,423,831 A | 6/1995 | Nates |
| 5,462,555 A | 10/1995 | Bolanos et al. |
| 5,564,262 A | 10/1996 | Bevis et al. |
| 5,609,599 A | 3/1997 | Levin |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,846,255 A | 12/1998 | Casey |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 | 4/2001 | Levinson |
| 6,228,097 B1 | 5/2001 | Levinson et al. |
| 6,273,253 B1 | 8/2001 | Forster et al. |
| 6,306,150 B1 | 10/2001 | Levinson |
| 6,349,727 B1 | 2/2002 | Stewart, Jr. |
| 6,391,035 B1 | 5/2002 | Appleby et al. |
| 6,419,682 B1 | 7/2002 | Appleby et al. |
| 6,421,920 B1 | 7/2002 | Jensen |
| 6,439,727 B1 | 8/2002 | Koide |
| 6,460,700 B2 | 10/2002 | Weisshaupt |
| 6,460,749 B1 | 10/2002 | Evinson et al. |
| 6,780,195 B2 | 8/2004 | Porat |
| 6,824,547 B2 | 11/2004 | Wilson, Jr. et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Iaconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 11,707,282 B2 | 7/2023 | Thomas et al. |
| 2002/0046961 A1 | 4/2002 | Levinson et al. |
| 2002/0177863 A1 | 11/2002 | Mandel et al. |
| 2004/0199178 A1 | 10/2004 | Small |
| 2005/0165423 A1 | 7/2005 | Gallagher et al. |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2009/0088783 A1 | 4/2009 | Kennedy et al. |
| 2009/0171380 A1 | 7/2009 | Whiting |
| 2011/0224700 A1 | 9/2011 | Schmidt et al. |
| 2011/0295291 A1 | 12/2011 | Trivisani |
| 2012/0083803 A1 | 4/2012 | Patel et al. |
| 2012/0226291 A1 | 9/2012 | Malizia et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2014/0025092 A1 | 1/2014 | Ewers et al. |
| 2014/0054192 A1 | 2/2014 | Chancibot |
| 2014/0236170 A1 | 8/2014 | Kethman et al. |
| 2014/0243862 A1 | 8/2014 | Bagaoisan et al. |
| 2014/0276970 A1 | 9/2014 | Messerly et al. |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0209151 A1 | 7/2017 | Brown |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0185029 A1 | 7/2018 | Lebens, III |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |
| 2019/0133590 A1 | 5/2019 | Richard |
| 2019/0159782 A1 | 5/2019 | Kamaraj et al. |
| 2019/0223874 A1 | 7/2019 | Pilletere et al. |
| 2020/0360021 A1 | 11/2020 | Foshee |

FOREIGN PATENT DOCUMENTS

| | | |
|---|---|---|
| CN | 106264647 A | 1/2017 |
| DE | 10116168 A1 | 11/2001 |
| EP | 3400887 A1 | 11/2018 |
| GB | 2353710 A | 3/2001 |

OTHER PUBLICATIONS

Partial European Search Report dated Nov. 13, 2020, issued in corresponding EP Appln. No. 20182582, 16 pages.

European Search Report dated Jan. 22, 2021, issued in corresponding EP Appln. No. 20182582, 17 pages.

European Office Action dated Oct. 19, 2023, issued in corresponding EP Application No. 20182582, 7 pages.

MULTI-PIECE LIGATION CLIP

CROSS-REFERENCE TO RELATED APPLICATION

This application is a divisional of U.S. patent application Ser. No. 16/866,649, filed May 5, 2020, which claims the benefit of and priority to U.S. Provisional Patent Application Ser. No. 62/869,584, filed Jul. 2, 2019, the entire contents of each of which are incorporated by reference herein.

BACKGROUND

Polymeric ligation clips typically include first and second beams that are coupled together at one end by a pivotable connection, e.g., living hinge, such that the first and second beams can be moved in relation to each other between open and clamped positions. The ligation clips can be applied to tissue endoscopically through a small diameter incision or through a small diameter cannula positioned through the incision to minimize trauma to a patient during a surgical procedure.

Typically, when polymeric clips are applied to tissue through a cannula and/or stored within an endoscopic clip applier, the clips are supported in a compressed or partially compressed state to minimize the overall dimension of the clips and facilitate delivery of the clips through the cannula or incision. Storing polymeric clips in a compressed or partially compressed state may impact the condition of the clips which may impact the performance of the clips. More specifically, storing the polymeric clips in a compressed or partially compressed state causes strain and/or material creep in the material of the polymeric clip, especially in the region of the living hinge, which may adversely impact the condition and/or performance of the polymeric clip.

SUMMARY

In one aspect of the disclosure, a ligation clip includes a first beam and a second beam. The first beam has a first end portion, a second end portion, and a clamping surface positioned between the first and second end portions. The first end portion includes a first mating feature and the second end portion includes a first locking structure.

The second beam has a first end portion, a second end portion, and a second clamping surface positioned between the first and second end portions. The first end portion of the second beam includes a second mating feature and the second end portion of the second beam includes a second locking structure. The second mating feature is adapted to be coupled to the first mating feature to couple the first beam to the second beam. The first beam is movable in relation to the second beam to move the ligation clip from an open position to a clamped position, wherein the first locking structure is adapted to engage the second locking structure to secure the ligation clip in the clamped position.

In aspects of the disclosure, the first mating feature includes a hook portion that defines a semi-cylindrical recess and the second mating feature includes a transverse post that is received within the semi-cylindrical recess to pivotably couple the first beam to the second beam.

In some aspects of the disclosure, the first end portion of the second beam defines a first through bore that receives the hook portion.

In certain aspects, the transverse post defines one end of the through bore.

In aspects of the disclosure, the second beam includes side walls, and the first end of the second beam defining a second through bore that extends between the side walls of the second beam, wherein the second through bore forms a flexible portion that is positioned to engage the first beam as the ligation clip is moved from the open position towards the clamped position to urge the ligation clip towards the open position.

In some aspects of the disclosure, the first mating feature includes a first body supporting a projection and the second mating feature includes a second body defining a first through bore that is dimensioned to receive the projection to couple the first beam to the second beam.

In certain aspects of the disclosure, the first body of the first mating feature defines a first flat surface that is contiguous with the first clamping surface of the first beam and the second body of the second mating feature defines a second flat surface that is contiguous with the second clamping surface of the second beam, wherein the first flat surface is in juxtaposed abutting relation with the second flat surface when the first and second mating features are coupled together.

In aspects of the disclosure, the first and second flat surfaces of the first and second mating features are oriented such that the ligation clip is in the open position in an undeformed condition when the first and second mating features are coupled together.

In some aspects of the disclosure, the projection is arrow-shaped and includes a retention head that has retention surfaces, wherein the retention surfaces are positioned to engage the second body of the second mating feature to obstruct removal of the projection from the first through bore.

In certain aspects of the disclosure, the first mating feature and the first locking structure each include a hook-shaped latch member and the second mating feature and the second locking structure each include a latch member receiver, wherein the hook-shaped latch members are movable into engagement with the respective latch member receivers to secure the ligation clip in the clamped position.

In aspects of the disclosure, the first beam includes a first boss positioned on each side of the second end portion of the first beam and the second beam includes a second boss positioned on each side of the second end portion of the second beam.

In some aspects of the disclosure, the first mating feature is adapted to be releasably coupled to the first mating structure.

In another aspect of the disclosure, a ligation clip includes a first beam and a second beam. The first beam has a first mating feature and defines a first clamping surface, and the second beam has a second mating feature and defines a second clamping surface. The second mating feature is coupled to the second mating feature to pivotably couple the first beam to the second beam such that the ligation clip is movable from an open position to a clamped position.

In the open position, the first beam is longitudinally aligned with the second beam and the first and second clamping surfaces face in a common direction.

In aspects of the disclosure, the first and second beams of the ligation clip are formed from a polymeric material.

In some aspects of the disclosure, the first and second mating features are configured to cause minimal strain on the first and second beams when the ligation clip is in the first position.

In certain aspects of the disclosure, each of the beams includes bosses that are adapted to support the ligation clip within a clip applier.

Another aspect of the disclosure is directed to a method of applying a ligation clip to tissue that includes supporting a first beam of the ligation clip having a first clamping surface on a first jaw of a tool assembly of a clip applier; supporting a second beam of the ligation clip having a second clamping surface on a second jaw of the tool assembly of the clip applier in a position in longitudinal alignment with the first beam; positioning the tool assembly of the clip applier adjacent tissue to be clamped; and moving the second jaw of the tool assembly in relation to the first jaw of the tool assembly to move the second beam of the ligation clip into juxtaposed alignment with the first beam of the ligation clip to move the ligation clip to a clamped position about the tissue.

In aspects of the disclosure, the method further includes advancing the tool assembly from a position within an elongate shaft of the clip applier to a position located externally of the elongate shaft the elongate shaft.

In some aspects of the disclosure, the first and second mating features are pivotally coupled to each other when the first and second beams of the ligation clip are supported within the elongate shaft of the clip applier.

In certain aspects of the disclosure, the method further includes moving an actuation rod of the clip applier from an advanced position to a retracted position to pivot the second jaw of the tool assembly in relation to the first jaw of the tool assembly.

Another aspect of the disclosure is directed to a clip applier including an elongate shaft and a tool assembly. The elongate shaft has a proximal end and a distal end. The tool assembly is supported on the distal end of the elongate shaft and includes a first jaw, a second jaw, and an actuator. The first jaw is pivotably coupled to the second jaw such that the tool assembly is movable between an open position and a clamped position. In the open position, the first jaw is in longitudinal alignment with the second jaw.

In some aspects of the disclosure, the first jaw is movable between the open position and the clamped position over an arc of about 180 degrees.

In certain aspects of the disclosure, the actuator is coupled to the first jaw and is movable within the elongate shaft to move the tool assembly between the open position and the clamped position.

In aspects of the disclosure, each of the first and second jaws includes a concavity for receiving a boss of a ligation clip.

Other features of the disclosure will be appreciated from the following description.

BRIEF DESCRIPTION OF THE DRAWINGS

Various aspects of the disclosed multi-piece ligation clip are described herein below with reference to the drawings, wherein.

DETAILED DESCRIPTION

Figure 1:
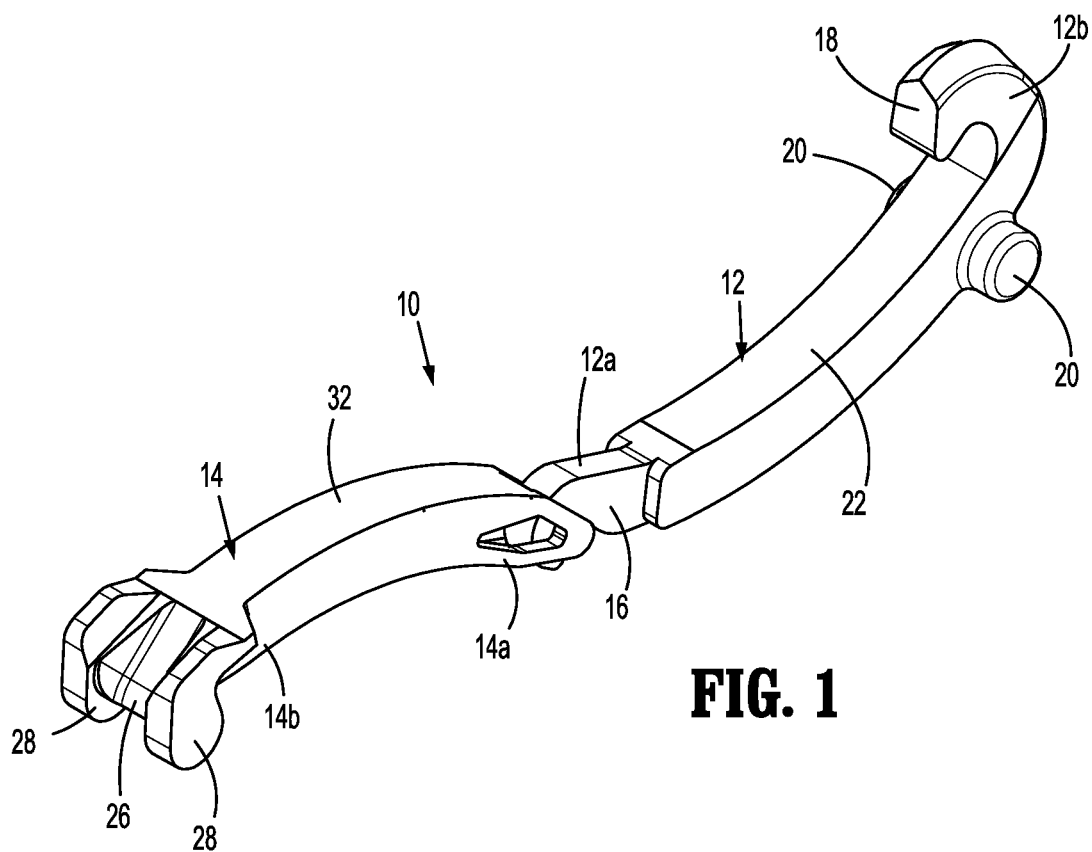
FIG. 1 is a side perspective view from the distal end of an exemplary embodiment of the disclosed multi-piece ligation clip with jaws of the clip coupled to each other and in an open position.

The disclosed ligation clip and ligation clip applier will now be described in detail with reference to the drawings in which like reference numerals designate identical or corresponding elements in each of the several views. However, it is to be understood that the disclosed aspects of the disclosed ligation clip are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, and support personnel. Finally, the term "substantially" or "about" is used generally to refer to 90 percent to 110 percent of a referenced parameter.

The disclosed ligation clip includes a first beam having a first end including a first mating feature and a second beam having a first end including a second mating feature. The first and second mating features of the first and second beams can be selectively coupled together to facilitate pivotable movement of the ligation clip between open and clamped positions. In aspects of the disclosed ligation clip, the first and second mating features are configured to allow the first and second beams to open to a position in which the first and second beams are substantially longitudinally aligned to minimize the outer dimension of the clip in the open position. In some aspects of the disclosed ligation clip, the first and second mating features are configured to minimize strain on the first and second beams when the clip is in the open position to minimize strain and material creep on the polymeric clip during storage and delivery of the ligation clip through a small diameter cannula.

Figure 2:
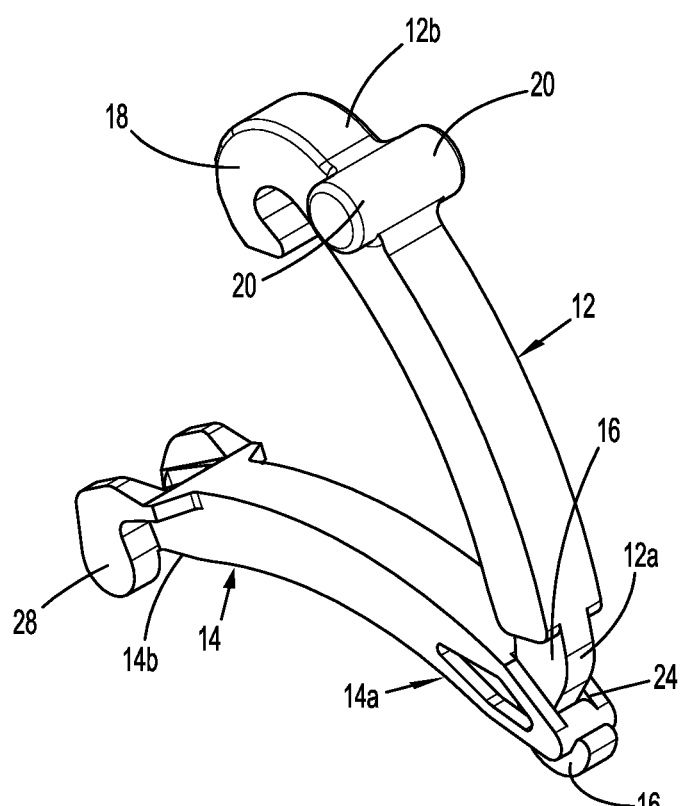
FIG. 2 is a side perspective view from the proximal end of the multi-piece ligation clip shown in FIG. 1 with jaws of the clip coupled to each other and in a partially open position.
Figure 3:
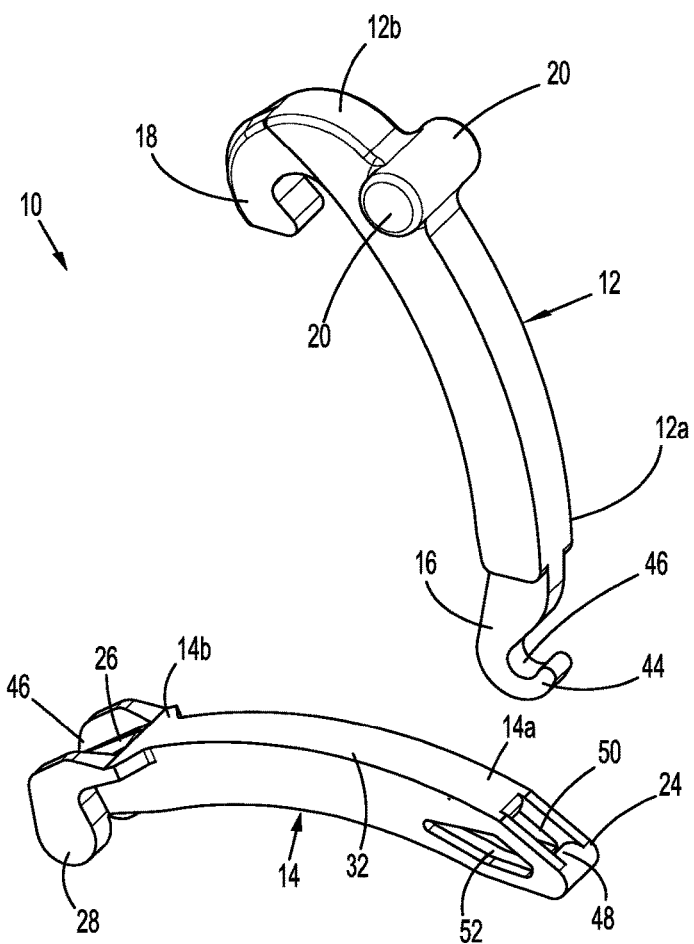
FIG. 3 is a side perspective view of the multi-piece ligation clip shown in FIG. 1 with the jaws of the ligation clip uncoupled from each other.

An exemplary embodiment of the disclosed polymeric ligation clip is shown in FIGS. 1-3 generally as ligation clip 10. The ligation clip 10 includes a first beam 12 and a second beam 14. The first beam 12 has a first end portion 12a including a first mating feature 16, and a second end portion 12b including a first locking element 18 and first bosses 20. The first bosses 20 extend from opposite sides of the first beam 12. In aspects of the disclosed ligation clip, the first bosses 20 can be formed from a single transverse member that is positioned on and extends across the first beam 12. Alternately, other beam configurations are envisioned. The first beam 12 has a first clamping surface 22 that faces the second beam 14 when the ligation clip 10 is moved to a clamped position.

Figure 7:
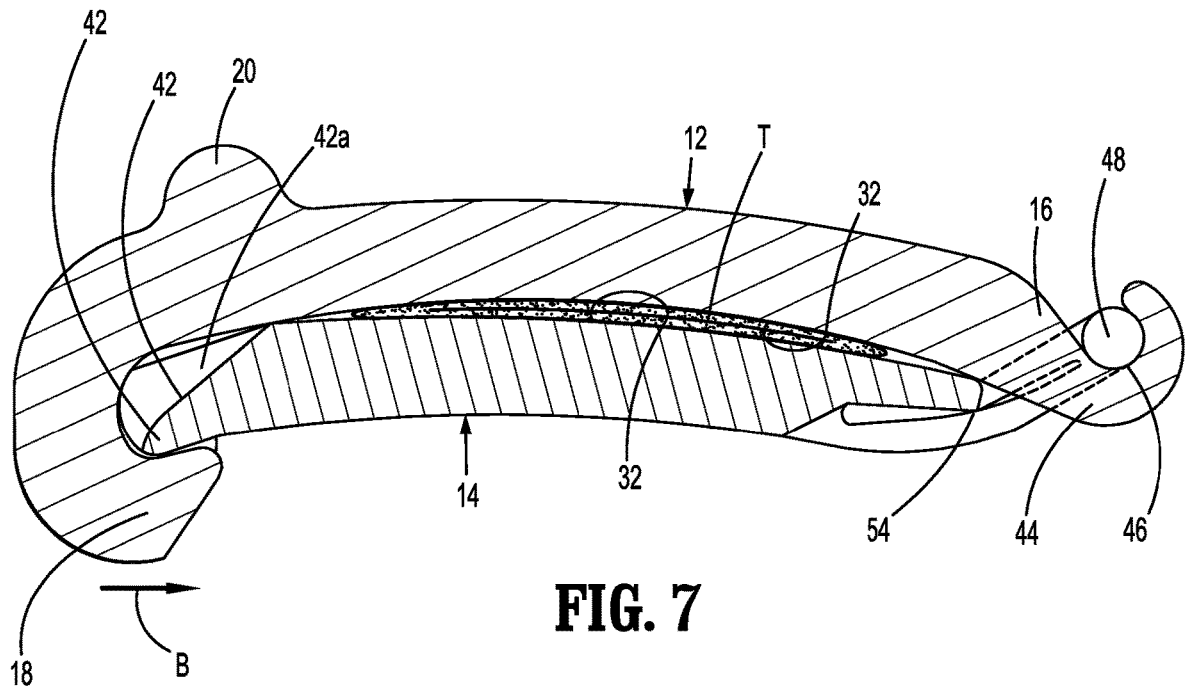
FIG. 7 is a side cross-sectional view of the multi-piece ligation clip shown in FIG. 6 in a clamped position.
Figure 8:
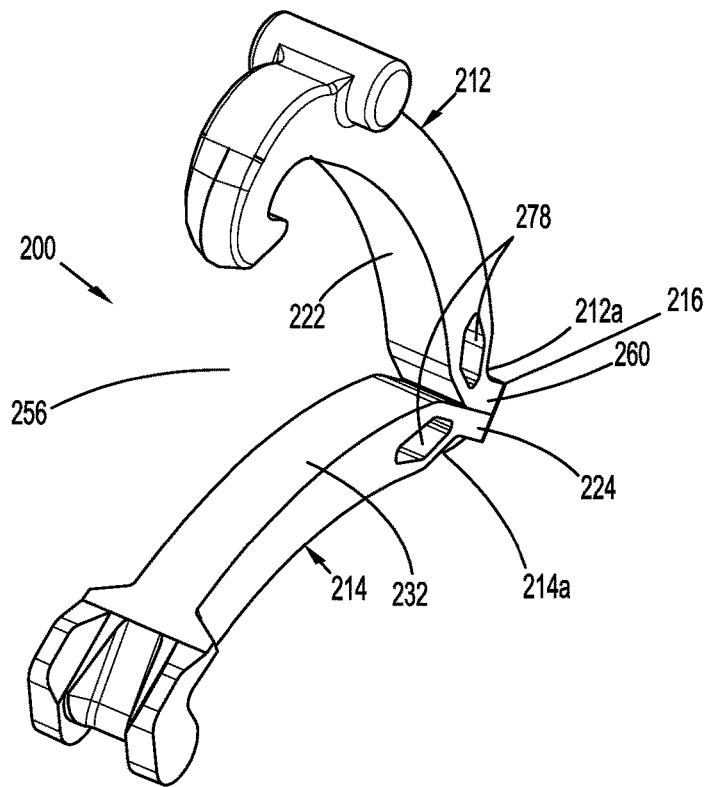
FIG. 8 is a side perspective view from the distal end of another exemplary embodiment of the disclosed multi-piece ligation clip with jaws of the clip coupled to each other and in an open position.
Figure 9:
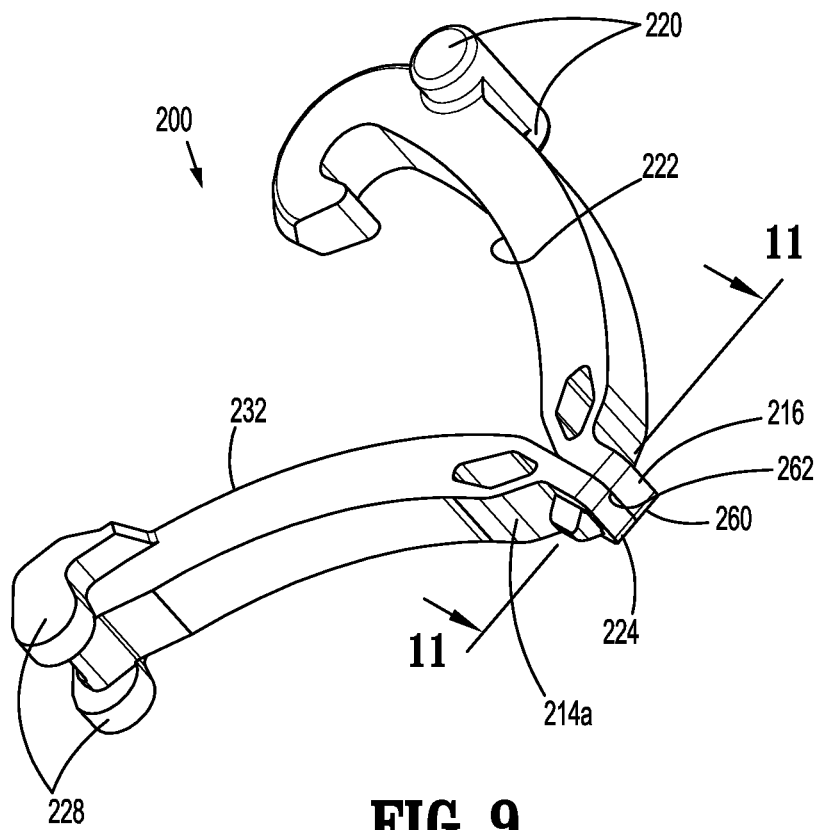
FIG. 9 is a side perspective view from the proximal end of the multi-piece ligation clip shown in FIG. 8 with jaws of the clip coupled to each other and in an open position.
Figure 10:
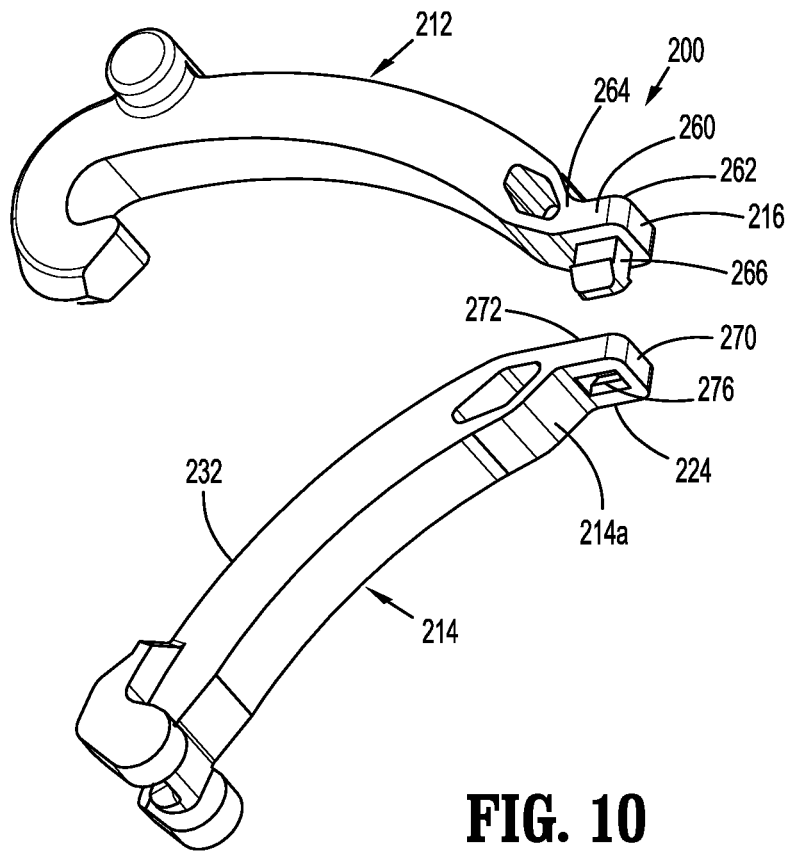
FIG. 10 is a side perspective view of the multi-piece ligation clip shown in FIG. 9 with the jaws uncoupled from each other.
Figure 11:
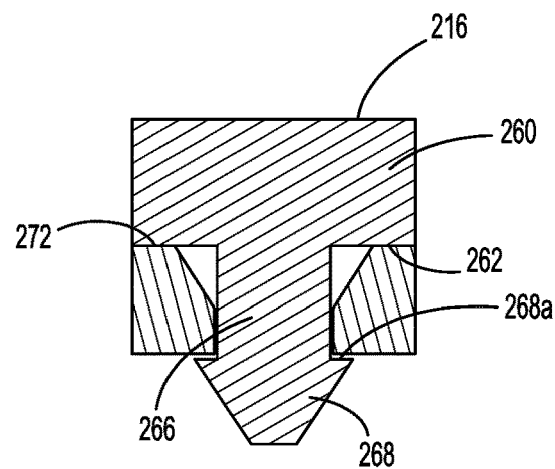
FIG. 11 is a cross-sectional view taken along section line 11-11 of FIG. 9.

The second beam 14 has a first end portion 14a including a second mating feature 24, and a second end portion 14b including a second locking element 26 and spaced second bosses 28. The second beam 14 has a second clamping surface 32 is in juxtaposed alignment with the first clamping surface 22 when the clip 10 is in the clamped position (FIG. 7). Although not illustrated herein, the first and second clamping surfaces 22 and 32 may include tissue retention features such as protrusions and/or recesses to minimize slippage of the ligation clip 10 along tissue when the ligation clip 10 is clamped about tissue. In the open position (FIG. 1), the first and second beams 12, 14 are longitudinally aligned and the clamping surfaces 22, 32 of the first and second beams 12, 14, respectively, face in substantially the same direction. In this position, no strain is placed on the first and second mating features 16, 24, respectively, of the first and second beams 12, 14, respectively.

In aspects of the disclosed ligation clip, the first locking element 18 of the first beam 12 includes a latch member 40 and the second locking element 26 of the second beam 14 includes a latch member receiver 42 that is positioned to receive and engage the latch member 40 to retain the ligation clip 10 in a clamped position (FIG. 7). In aspects of the disclosed ligation clip, the latch member 40 may be hook-shaped and the latch member receiver 42 may define a channel 42a between the second bosses 28 that directs or guides the latch member 40 into engagement with the latch member receiver 42. Alternately, the first and second locking elements 18 and 26 may assume a variety of different configurations to retain the ligation clip 10 in the clamped position (FIG. 7).

FIG. 3 illustrates the ligation clip 10 with the first beam 12 separated from the second beam 14. As illustrated, the first mating feature 16 of the first beam 12 of the ligation clip 10 is configured to be coupled with the second mating feature 24 of the second beam 14 of the ligation clip 10 to facilitate pivotable movement of the first beam 12 in relation to the second beam 14 between open (FIG. 1) and clamped positions (FIG. 7). In aspects of the disclosed ligation clip, the first mating feature 16 of the first beam 12 includes a hook portion 44 that defines a semi-cylindrical recess 46 and the second mating feature 24 includes a transverse post 48 that can be received within the semi-cylindrical recess 46 to couple the first beam 12 to the second beam 14. In aspects of the disclosed ligation clip, the transverse post 48 (FIG. 5) is substantially cylindrical.

In some aspects of the disclosed ligation clip, the first end portion 14a of the second beam 14 defines a first through bore 50 that extends through an upper surface of the beam 14 that is contiguous with the second clamping surface 32 and receives the hook portion 44 of the first beam 12. The transverse post 48 defines one end of the first through bore 50 and is received within the semi-cylindrical recess 46 of the hook portion 44 of the first mating feature 16 when the hook portion 44 is inserted through the first through bore 50 of the second beam 14 to pivotably secure the first beam 12 to the second beam 14. The configuration of the first and second mating features 16 and 24 allows the ligation clip 10 to be positioned in the open position with the first beam 12 in substantial alignment with the second beam 14 without placing any strain on the first and second mating features 16 and 24 of the first and second beams 12, 14 to minimize strain and material creep within the ligation clip 10.

In aspects of the disclosed ligation clip, the second beam 14 of the ligation clip 10 also defines a second through bore 52 that extends between side walls of the second beam 14. The second through bore 52 allows a portion of the first end portion 14a of the second beam 14 to flex inwardly upon movement of the ligation clip 10 to the clamped position to facilitate closure of the ligation clip 10. In aspects of the disclosed ligation clip, the second through bore 52 may have a diamond shape to form a flexible portion 54 (FIG. 5) on the first end 14a of the second beam 14. Alternately, other configurations are envisioned for the second through bore 52, e.g., oval, circular, etc.

FIGS. 4-7 illustrate the ligation clip 10 supported in a conventional clip applier 100 as the ligation clip 10 in moved from a partially open position (FIG. 4) to the clamped position (FIG. 7) to apply the ligation clip 10 to tissue. It is noted that the ligation clip 10 is shown in the fully open position supported on a clip applier 500 in accordance with an exemplary embodiment of the disclosure in FIGS. 19-25 which are described in detail below. The clip applier 100 includes a first jaw 102 and a second jaw 104 that is secured to the first jaw 102 by a pivot member 106. The pivot member 106 facilitates pivotal movement of the first jaw 102 in relation to the second jaw 104 between an open position (FIG. 4) and a closed position. The jaws 102 and 104 include semi-circular recesses 108a and 108b that receive the first and second bosses 20 and 28 of the first and second beams 12 and 14, respectively, to support the ligation clip 10 between the jaws 102, 104. Receipt of the bosses 20 and 28 within the recesses 108a and 108b secures the ligation clip 10 between the jaws 102 and 104.

Figure 4:
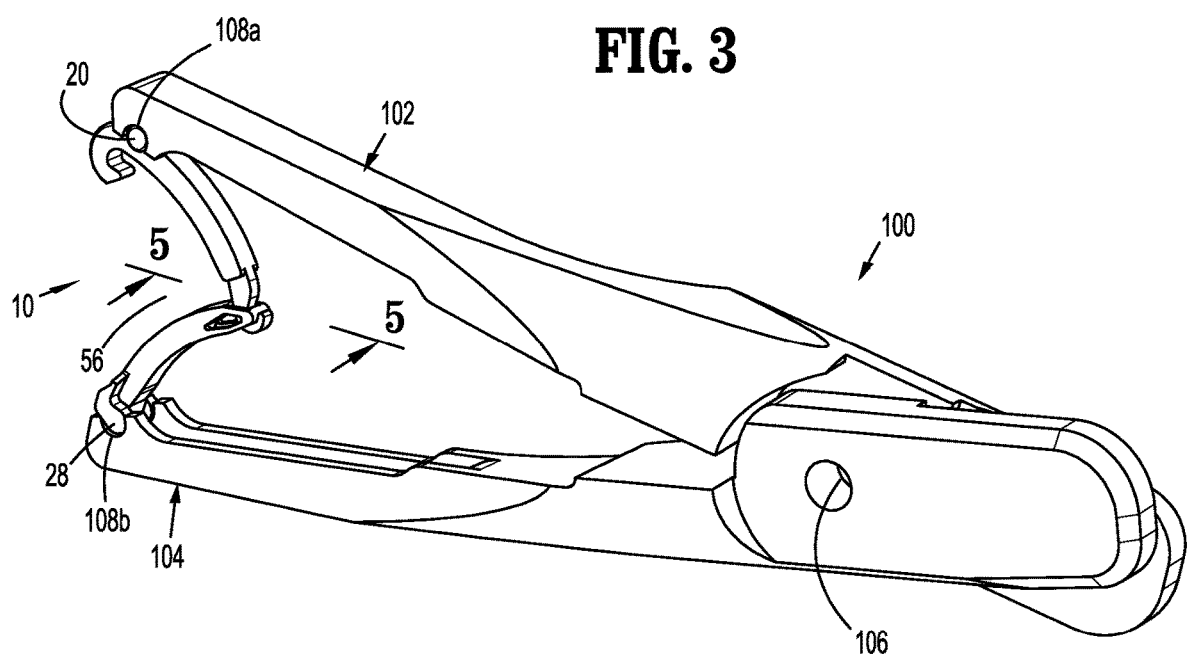
FIG. 4 is a side perspective view the multi-piece ligation clip shown in FIG. 1 with the jaws of the clip coupled to each other and in an open position, and the clip supported between jaws of a clip applicator.
Figure 5:
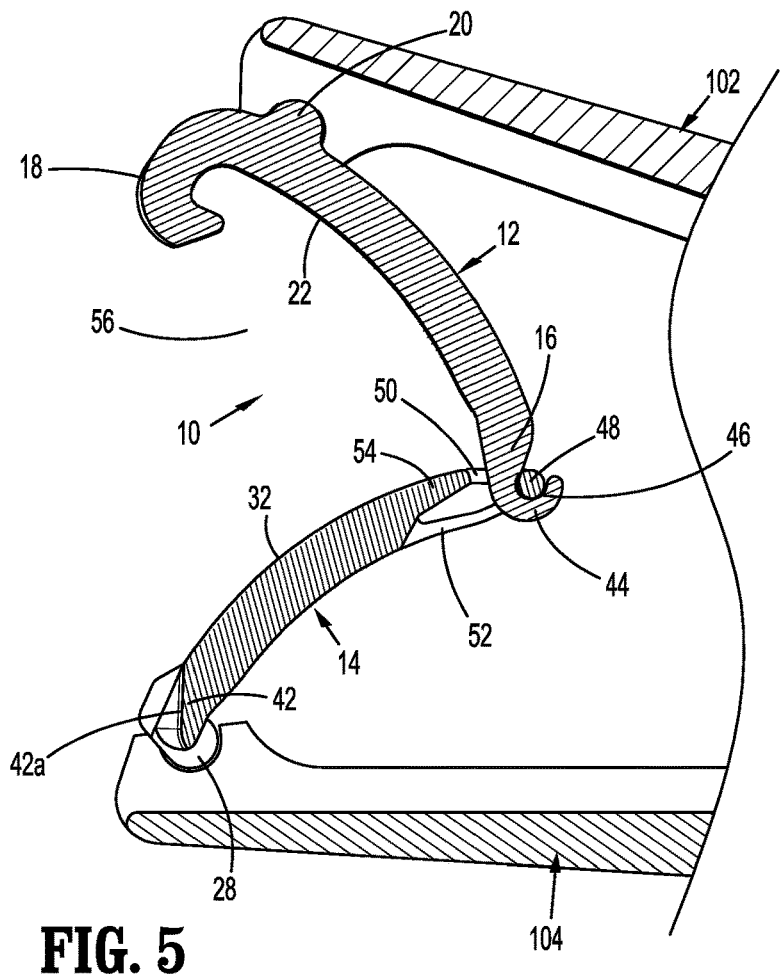
FIG. 5 is a cross-sectional view taken along section line 5-5 of FIG. 4.

FIGS. 4 and 5 illustrate the ligation clip 10 supported between the first and second jaws 102 and 104 of the clip applier 100 in an open position. In this position, the bosses 20 are received within the recesses 108a in the jaw 102 of the clip applier 100 and the bosses 28 are received in the recesses 108b in the jaw 104 of the clip applier 100. The first clamping surface 22 on the second end portion 12b of the first beam 12 is spaced from the second clamping surface 32 on the second end portion 14b of the second beam 14 such that the first locking element 18 is spaced from the second locking element 26. In this position, the second ends 12b and 14b of the first and second beams 12 and 14 define a mouth 56 for receiving tissue "T" (FIG. 7) and the flexible portion 54 (FIG. 5) of the first end 14a of the second beam 14 is not compressed such that minimal strain is applied to the first and second beams 12, 14.

Figure 6:
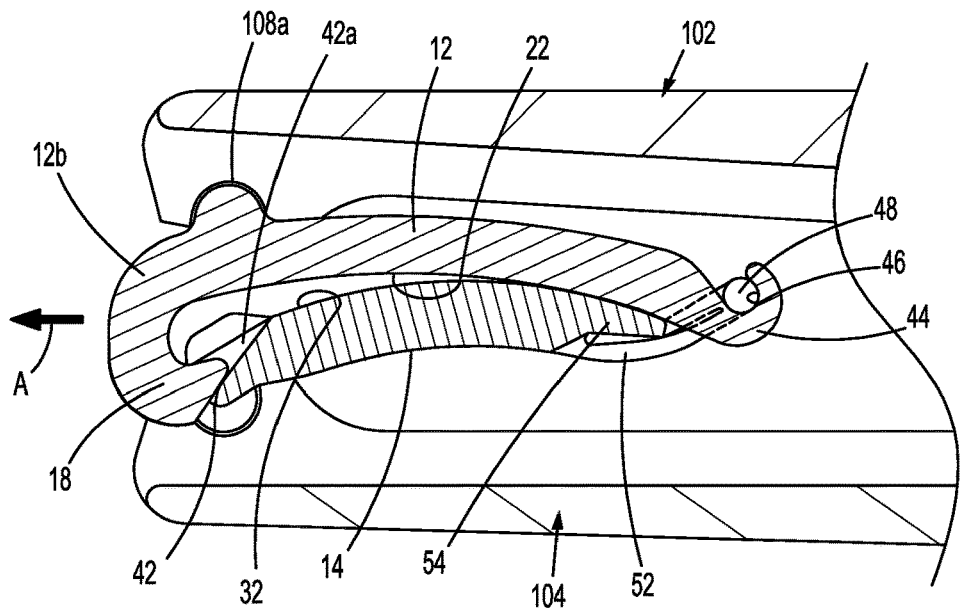
FIG. 6 is a side cross-sectional view of the multi-piece ligation clip and clip applicator shown in FIG. 4 with as the jaws of the clip are moved towards a clamped position.

FIGS. 6 and 7 illustrate the ligation clip 10 and clip applier 100 as the jaws 102 and 104 of the clip applier 100 are approximated to move the ligation clip 10 from the open position towards the clamped position. As illustrated, as the first beam 12 approaches the second beam 14, the first clamping surface 22 of the first beam 12 engages the flexible portion 54 of the second beam 14 to flex the flexible portion 54 downwardly to decrease the size of the through bore 52 in the side walls of the second beam 14. As the ligation clip 10 approaches the clamped position (FIG. 7), the first locking element 18 moves through the channel 42a defined in the latch member receiver 42. As the first locking element 18 moves through the channel 42a of the latch member receiver 42, contact between the first locking element 18 and the second locking element 26 biases the first locking element 18 outwardly in the direction indicated by arrow "A" in FIG. 6 to allow the first locking element 18 to pass over and snap into engagement with the locking member receiver 42 in the direction indicated by arrow "B" in FIG. 7. In this position, the tissue "T" (FIG. 7) is clamped between the first and second clamping surfaces 22 and 32 of the first and second beams 12 and 14, respectively. The flexible portion 54 on the first end portion 14a of the second beam 14 remains compressed and urges the first and second beams 12 and 14 to the open position. This force helps to retain the first and second locking elements 18 and 26 engaged with each other to retain the ligation clip 10 in the clamped position.

FIGS. 8-14 illustrate another exemplary embodiment of the disclosed ligation clip shown generally as 200. The ligation clip 200 is substantially similar to the ligation clip 10 except for the configuration of the first mating feature 216 on the first beam 212 and the configuration of the second mating feature 224 on the second beam 214. Accordingly, for the sake of brevity, only the first and second mating features 216 and 224 will be described in detail herein.

Figure 14:
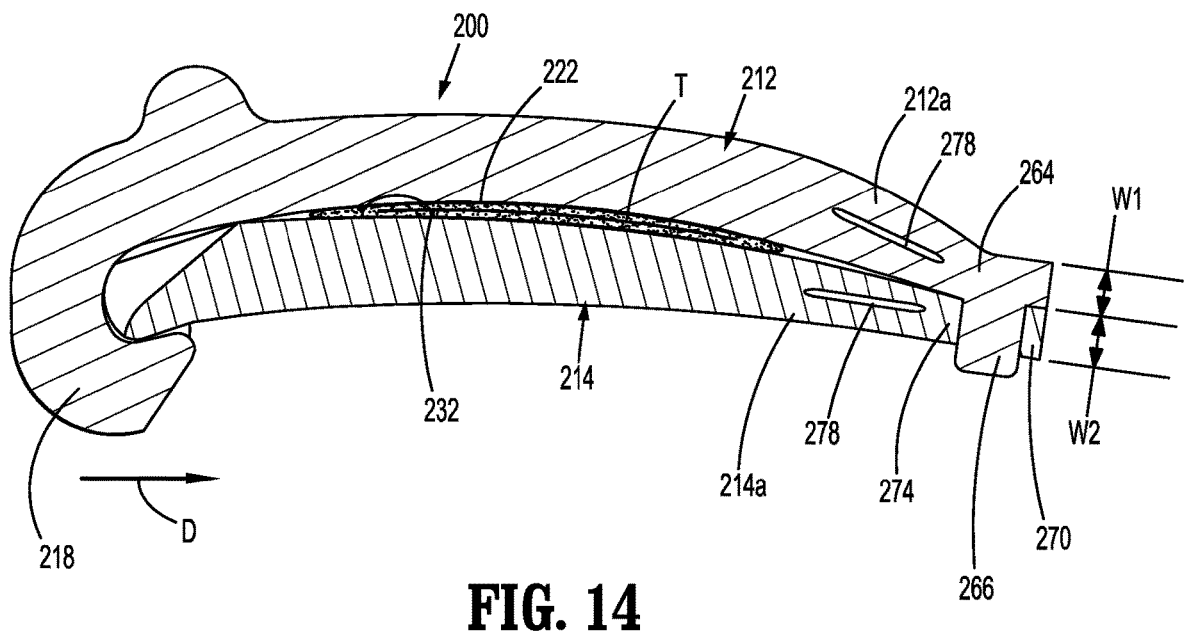
FIG. 14 is a cross-sectional view of the multi-piece ligation clip shown in FIG. 13 in the clamped position.

FIGS. 8-11 illustrate the ligation clip 200 in the open position with the second end portion of the first beam 212 spaced from the second end portion 214a of the second beam 214 to define a mouth 256 for receiving tissue "T" (FIG. 14). As described above in regard to the ligation clip 10 (FIG. 1), the first beam 212 includes a first clamping surface 222 and the second beam 214 includes a second clamping surface 232. The first mating feature 216 is formed on the first end 212a of the first beam 212 and includes a body 260 defining a flat surface 262 that is contiguous with the first clamping surface 222. The body 260 has a width "W1" (FIG. 14) that is substantially less than the width of the first beam 212 to define a living hinge 264 that facilitates pivotal movement of the first clamping surface 222 in relation to the body 260. The body 260 includes a projection 266 that extends downwardly from the flat surface 262 towards the second beam 214. The projection 266 is arrow-shaped and includes a retention head 268 that having retention surfaces 268a.

The second mating feature 224 is formed on the first end 214a of the second beam 214 and includes a body 270 defining a flat surface 272 that is contiguous with the second clamping surface 232. The body 270 has a width "W2" that is substantially less than the width of the second beam 214 to define a living hinge 274 that facilitates pivotal movement of the second clamping surface 232 in relation to the body 270. The body 270 defines a first through bore 276 (FIG. 10) that is dimensioned to receive the projection 266 of the first mating feature 216 to secure the first end portion 214a of the second beam 214 to the first end portion 212a of the first beam 212. When the first mating feature 216 of the first beam 212 is secured to the second mating feature 224 of the second beam 214, the flat surface 262 of the first mating feature 216 is positioned in juxtaposed engagement with the flat surface 272 of the second mating feature 224 of the second beam 214. In this position, with the first and second beams 212 and 214, respectively, in undeformed conditions, the ligation clip 200 is in an open position (FIG. 8) with minimal strain placed on the first and second beams 212, 214.

The first end of each of the first and second beams 212 and 214 includes a second through bore 278 that extends between side walls of the first and second beams 212 and 214. The second through bores 278 allow a portion of the first end portions 212a and 214a of the first and second beams 212 and 214, respectively, to flex inwardly upon movement of the ligation clip 200 towards the clamped position to facilitate closure of the ligation clip 200. In aspects of the disclosed ligation clip, the first and second through bores 278 may have diamond shapes although other configurations are envisioned, e.g., oval, circular, etc.

Figure 12:
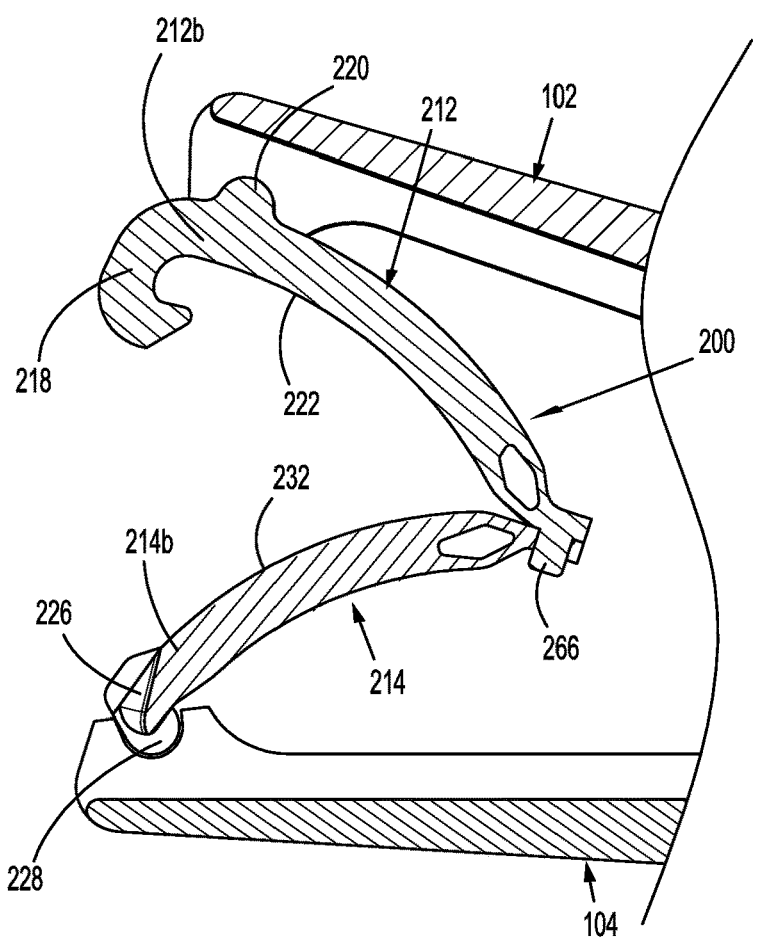
FIG. 12 is a cross-sectional view of the multi-piece ligation clip shown in FIG. 9 supported between the jaws of a clip applicator in the open position.

FIG. 12 illustrates the ligation clip 200 supported between the first and second jaws 102 and 104 of the clip applier 100 (FIG. 4) in an open position. In this position, bosses 220 on the first beam 212 of the ligation clip 200 are received within the recesses 108a in the jaw 102 of the clip applier 100 and the bosses 228 on the second beam 214 of the ligation clip 200 are received in the recesses 108b in the jaw 104 of the clip applier 100. The first clamping surface 222 on the second end portion 212b of the first beam 212 is spaced from the second clamping surface 232 on the second end portion 214b of the second beam 214 such that the first locking element 218 is spaced from the second locking element 226. In this position, minimal strain is placed on the first and second beams 212 and 214.

Figure 13:
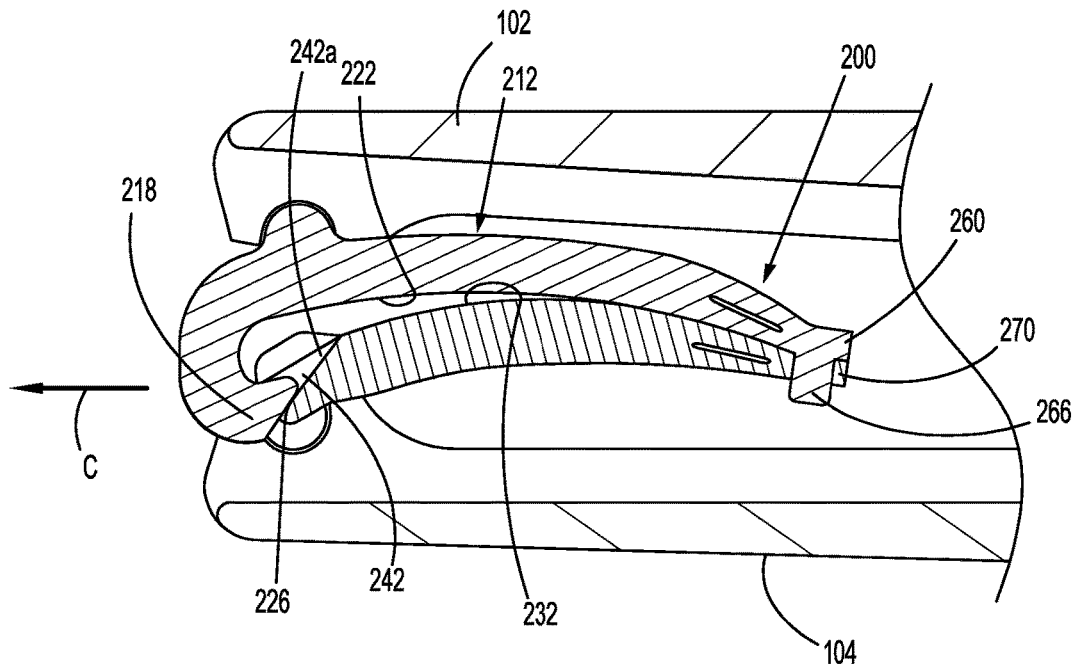
FIG. 13 is a cross-sectional view of the multi-piece ligation clip shown in FIG. 12 supported between the jaws of a clip applicators the jaws of the clip are moved towards the clamped position.

FIGS. 13 and 14 illustrate the ligation clip 200 and clip applier 100 (FIG. 4) as the jaws 102 and 104 of the clip applier 100 (FIG. 4) are approximated to move the ligation clip 200 from the open position (FIG. 12) towards the clamped position (FIG. 14). As illustrated, as the first beam 212 approaches the second beam 214, the first and second beams 212 and 214 bend at their hinge portions 264 and 274, respectively, such that the clamping surfaces 222 and 232 of the first and second beams 212 and 214 move into juxtaposed alignment. As the ligation clip 200 approaches the clamped position (FIG. 13), the first locking element 218 of the first beam 212 moves through the channel 242a (FIG. 13) defined in the latch member receiver 242. As the first locking element 218 moves through the channel 242a of the latch member receiver 242, contact between the first locking element 218 and the second locking element 226 biases the first locking element 218 outwardly in the direction indicated by arrow "C" in FIG. 13 to allow the first locking element 218 to pass over and snap into engagement with the second locking element 226 in the direction indicated by arrow "D" in FIG. 14. In this position tissue "T" is clamped between the first and second clamping surfaces 222 and 232 of the first and second beams 212 and 214, respectively. As described above, the first and second beams 212, 214, respectively, are deformed about their hinge portions 264 and 274, respectively, to generate a force in the beams 212 and 214 tending to urge the beams 212 and 214 to the open position (FIG. 12). This force helps to retain the first and second locking elements 218 and 226 engaged with each other to retain the ligation clip 200 in the clamped position.

Although the beams 212, 214 of the ligation clip 200 are illustrated as being coupled together during delivery of the ligation clip 200 to a surgical site, it is envisioned that the first and second beams 212, 214 (as well as beams 12, 14 of ligation clip 10) could be delivered to a surgical site as separate components and coupled together upon delivery to the surgical site prior to being moved to the clamped position. This would allow the first and second beams 212, 214 to be delivered to the surgical site with the first beam 212 longitudinally aligned with the second beam 214 (such as shown in FIG. 1 in regard to ligation clip 10) to facilitate delivery of the ligation clip 200 through a small diameter cannula or incision.

FIGS. 15-18 illustrate another exemplary embodiment of the disclosed ligation clip shown generally as 300. The ligation clip 300 is substantially similar to the ligation clip 10 (FIG. 1) and 200 (FIG. 8) except for the configuration of the first mating feature 316 on the first beam 312 and the configuration of the second mating feature 324 on the second beam 314. Accordingly, for the sake of brevity, only the first and second mating features 316 and 324 will be described in detail herein.

Figure 15:
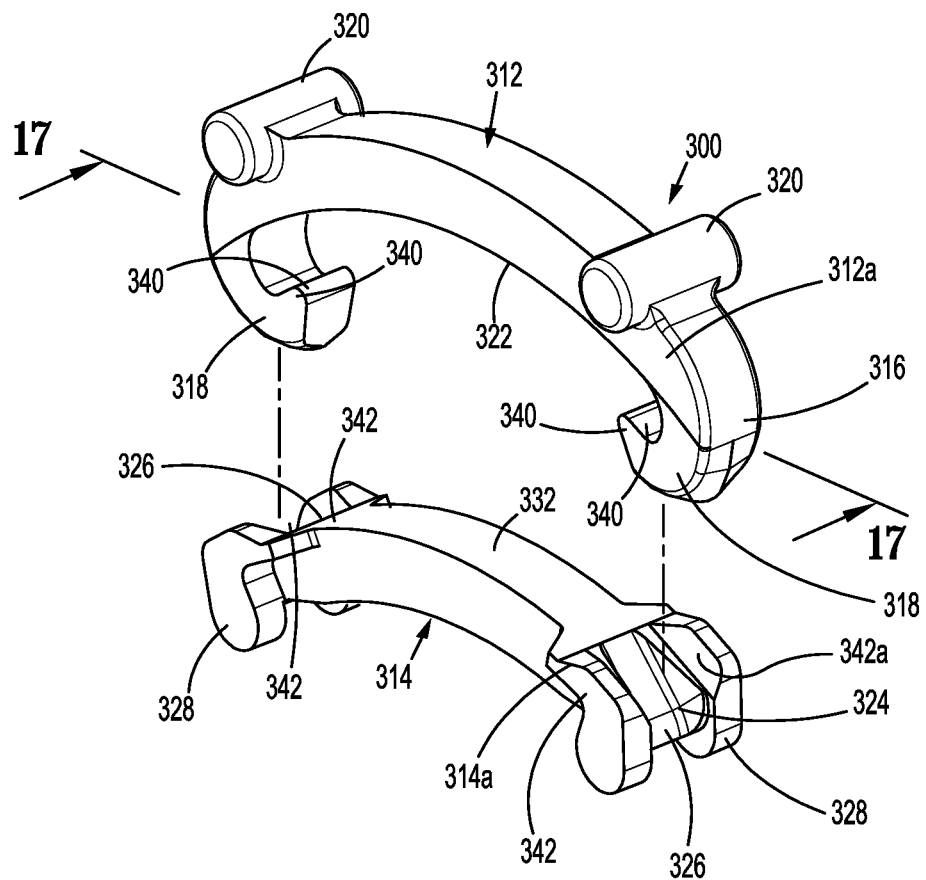
FIG. 15 is a side perspective view from the distal end of another exemplary embodiment of the disclosed multi-piece ligation clip with jaws of the clip uncoupled from each other.

FIG. 15 illustrates the ligation clip 300 in the open position with the first beam 312 spaced from the second beam 314. In contrast to the ligation clips 10 (FIG. 1) and 200 (FIG. 8) described above, the first and second beams 312 and 314, respectively, of the ligation clip 300 are not pivotably coupled to each other at one end. Rather, the first and second beams 312 and 314 are moved to the closed position in parallel orientation to clamp tissue "T" (FIG. 18. As described above in regard to the ligation clips 10 and 200, the first beam 312 of the ligation clip 300 includes a first clamping surface 322 and the second beam 314 of the ligation clip 300 includes a second clamping surface 332.

Figure 16:
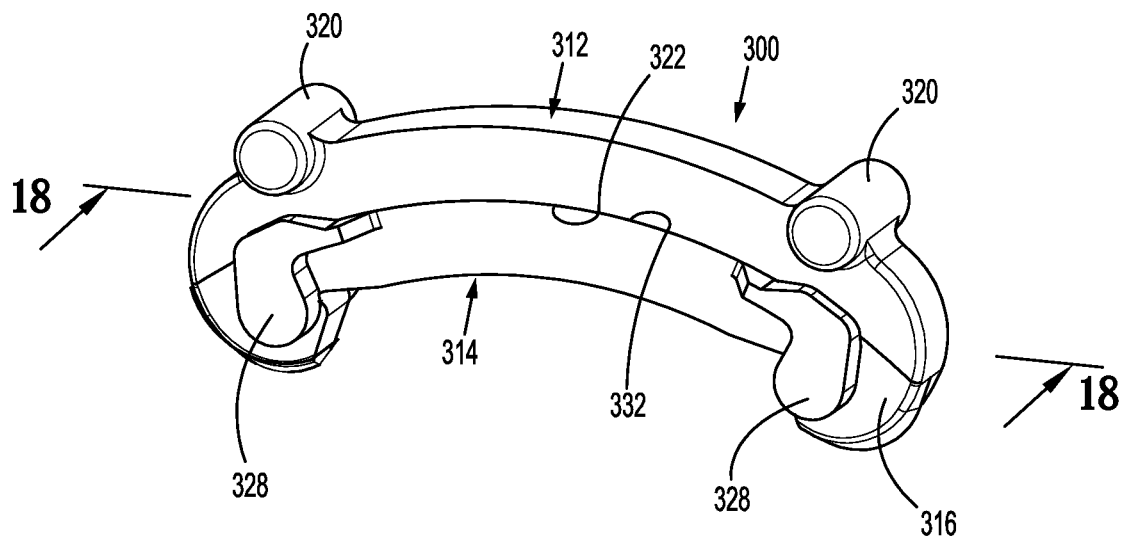
FIG. 16 is a side perspective view from the distal end of the multi-piece ligation clip shown in FIG. 15 with jaws of the clip coupled to each other and the clip in a clamped position.

The first mating feature 316 on the first end portion 312a of the first beam 312 is substantially similar to the first locking element 318 on the second end portion 312b of the first beam 312. More specifically, in the ligation clip 300, each end of the first beam 312 includes a first locking element 318. As described above in regard to locking element 18 (FIG. 1) of ligation clip 10, the locking element 318 includes a latch member 340 that is hook-shaped. Similarly, the second mating feature 324 on the first end 314a of the second beam 314 is substantially similar to the second locking element 326 on the second end of the second beam 314. More specifically, in the ligation clip 300, each end of the second beam 314 includes a second locking element 326. As described above in regard to locking element 26 of ligation clip 10 (FIG. 1), the second locking elements 326 on each end of the second beam 314 each include a latch member receiver 342 that is positioned to receive and engage one of the latch members 340 of the first locking element 318 to secure the first beam 312 in relation to the second beam 314 to retain the ligation clip 300 in a clamped position (FIG. 16). In aspects of the disclosed ligation clip, the latch member receivers 342 define channels 342a between the second bosses 328 that direct or guide the latch members 340 into engagement with the latch member receivers 342. The first beam 312 includes bosses 320.

Figure 17:
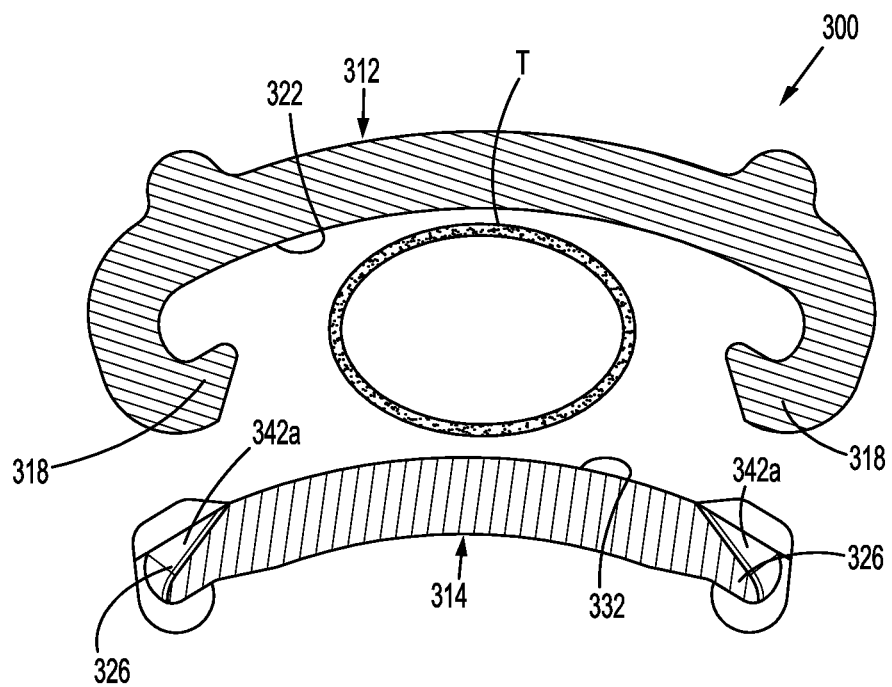
FIG. 17 is a cross-sectional view taken along section line 17-17 of FIG. 15.
Figure 18:
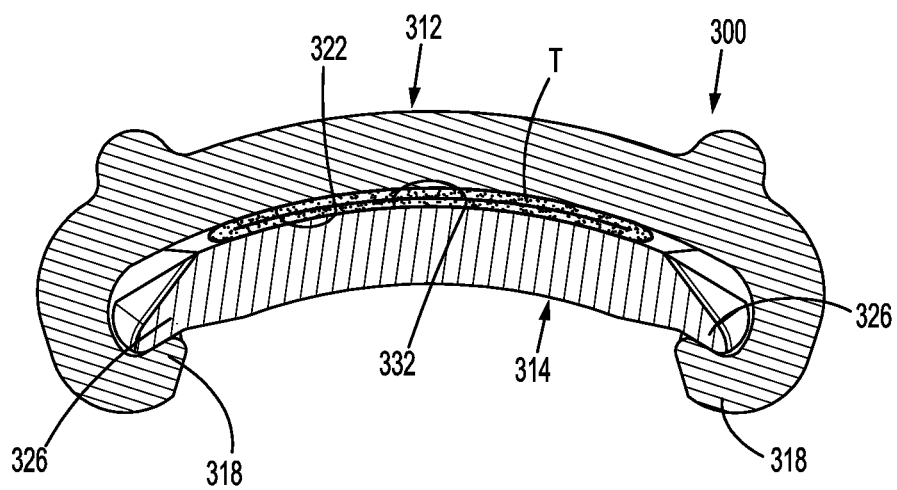
FIG. 18 is a cross-sectional view taken along section line 18-18 of FIG. 16.
Figure 19:
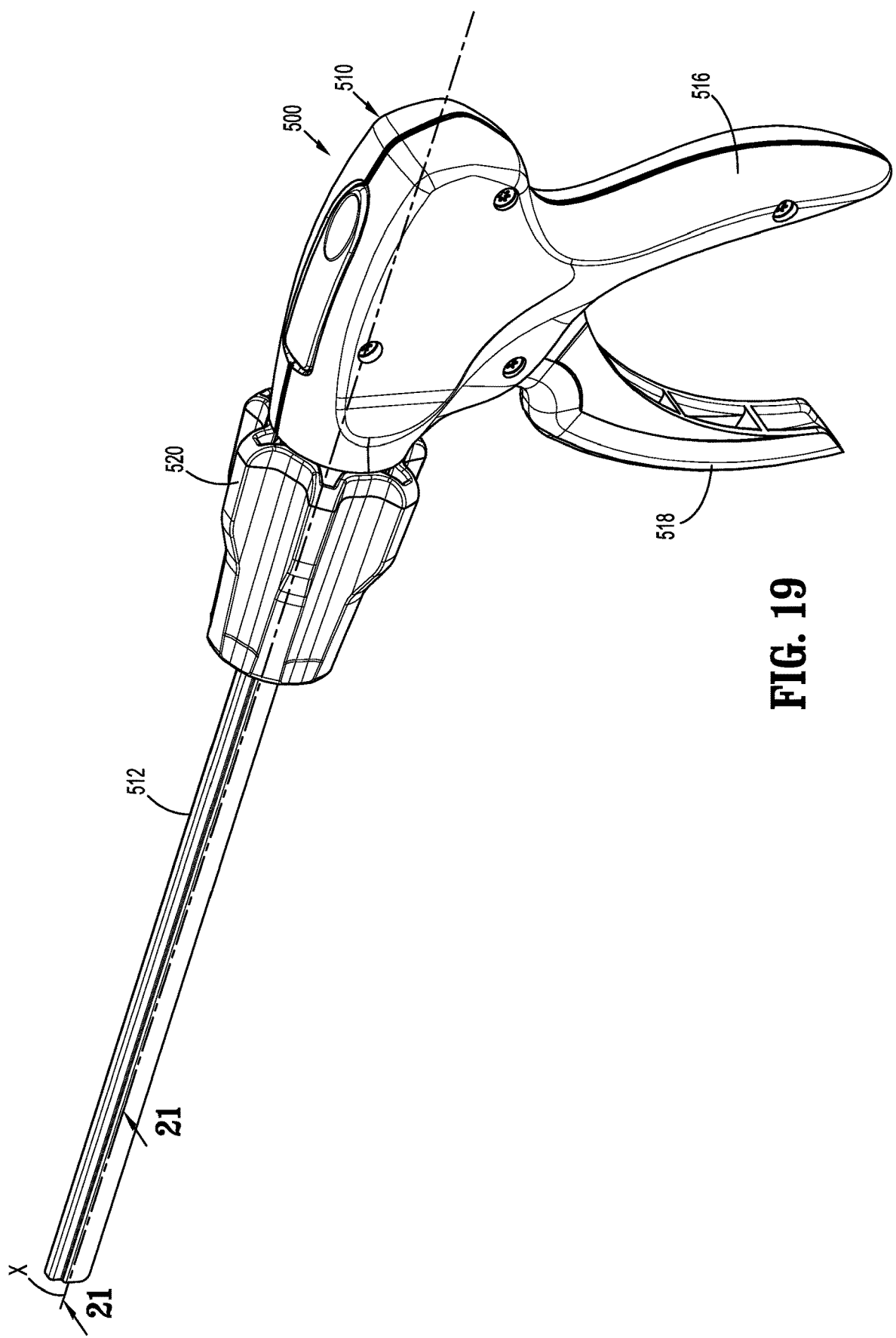
FIG. 19; is a side perspective view of an exemplary embodiment of a clip applier for applying a ligation clip to tissue.

FIGS. 17 and 18 illustrate the ligation clip 300 as the ligation clip 300 is clamped about tissue "T". When the ligation clip 300 is positioned about the tissue "T", the first beam 312 is positioned on one side of the tissue "T" and the second beam 314 is positioned on an opposite side of the tissue "T" with the first locking elements 318 aligned with the second locking elements 326. Next, the first and second beams 312 and 314 are brought together to the clamp the tissue "T" between the first and second clamping surfaces 322 and 332. As discussed above, when the first locking elements 318 engage the second locking elements 326, the first locking elements 318 move through the channels 342a defined in the latch member receivers 342. As the first locking elements 318 move through the channels 342a of the latch member receivers 342, contact between each of the first locking elements 318 and a respective one of the second locking elements 326 biases the first locking elements 318 outwardly to allow the first locking elements 318 to pass over and snap into engagement with the locking member receiver 342 (FIG. 18). Engagement between the first and second locking elements 318 and 326 secures the first beam 312 to the second beam 314 in the clamped position. As described above, the first and second beams 312, 314 can be delivered to a surgical site independently with the beams 312, 314 in longitudinal alignment to facilitate delivery of the ligation clip through a small diameter incision or trocar.

Figure 20:
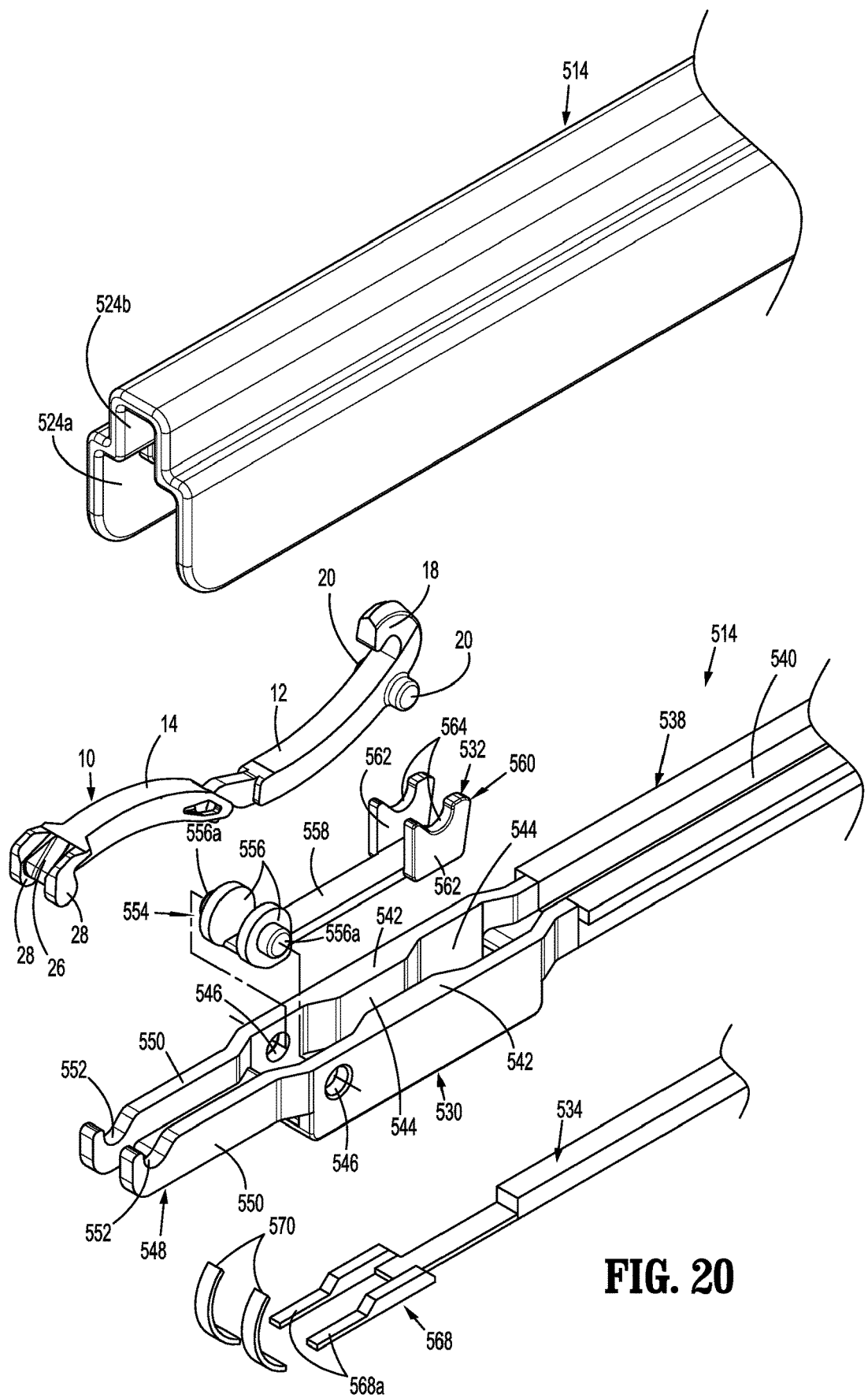
FIG. 20 is a side perspective view of a distal portion of the clip applier shown in FIG. 19 with the multi-piece ligation clip shown in FIG. 1 with parts separated.

FIGS. 19-24 illustrate a surgical clip applier, shown generally as clip applier 500, that can be used to apply a surgical clip, e.g., ligation clip 10 (FIG. 1), to tissue "T". The clip applier 500 includes a handle assembly 510, an elongate shaft 512 that defines a longitudinal axis "X", and a tool assembly 514 (FIG. 20). The handle assembly 510 includes a stationary handle 516 and a movable trigger 518 that is movable from a non-compressed position (FIG. 19) toward the stationary handle 516 to a compressed position to operate the tool assembly 514 (FIG. 20). In aspects of the disclosed ligation clip, the elongate shaft 512 includes a proximal portion that is supported by a scalloped rotation knob 520. The scalloped rotation knob 520 is supported on the handle assembly 510 for rotation such that rotation of the rotation knob 520 about the longitudinal axis "X" causes rotation of the elongate shaft 512 and tool assembly 514 in relation to the handle assembly 510 about the longitudinal axis "X".

The elongate shaft 512 defines a stepped channel 524 that extends from the handle assembly 510 and receives the tool assembly 514. The stepped channel 524 has a first portion 524a and a second portion 524b having a width that is smaller than the width of the first portion 524a. The tool assembly 514 is received within the first portion 524a of the stepped channel 524 and is movable from a retracted position within the stepped channel 524 (FIG. 21) to an advanced position (FIG. 22) extending from a distal end of the stepped channel 524. The ligation clip 10 extends into and is partially received within the second portion 524b of the stepped channel 524. Engagement between the ligation clip 10 and walls defining the second portion 524b of the stepped channel 524 maintains the orientation of the ligation clip 10 within the stepped channel 524 and on the tool assembly 514 as the tool assembly 514 is moved within the stepped channel 524 from its retracted position to its advanced position.

Figure 21:
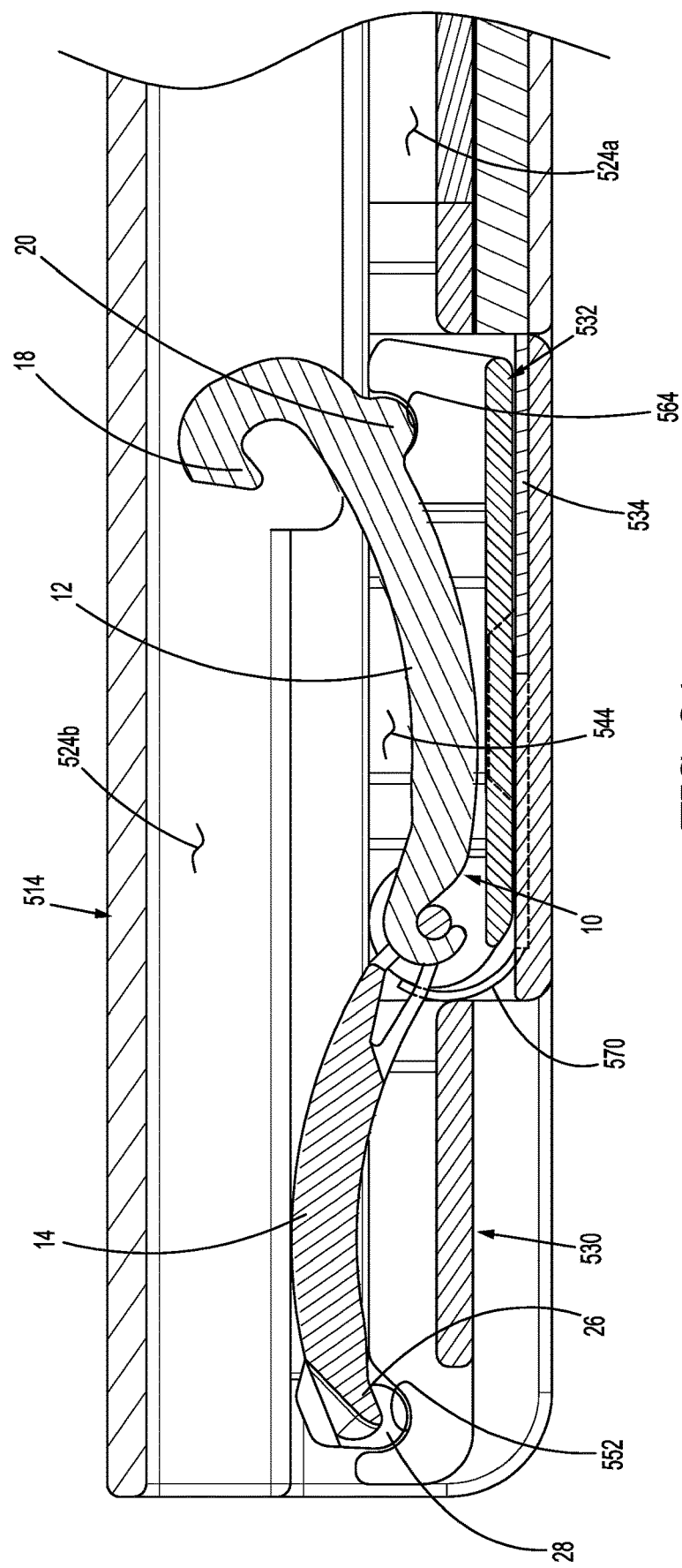
FIG. 21 is a cross-sectional view taken along section line 21-21 of FIG. 19.
Figure 22:
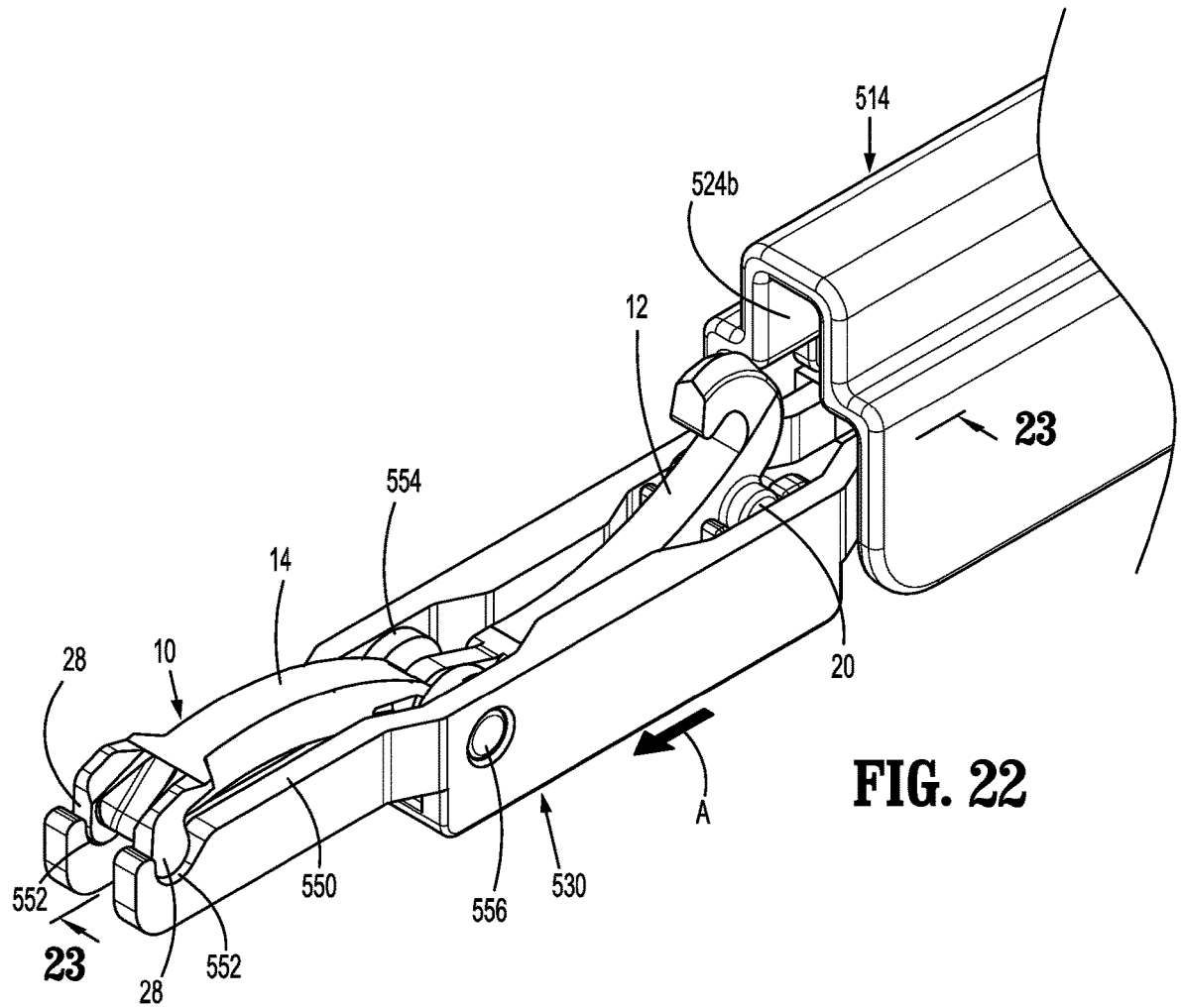
FIG. 22 is a side perspective view of the distal portion of the clip applier shown in FIG. 19 with a tool assembly in an advanced open position.

FIGS. 20 and 21 illustrate the tool assembly 514 which includes a first jaw 530, a second jaw 532, and an actuator rod 534. The first jaw 530 supports the second jaw 532 and is movable longitudinally within the first portion 524a of the stepped channel 524 between its retracted position (FIG. 21) and its advanced position (FIG. 22). The first jaw 530 is supported on a distal end portion of a rail 538 that extends from the handle assembly 510 through the elongate shaft 512. The rail 538 defines a channel 540 that receives the actuator rod 534. The stationary jaw 530 includes side walls 542 that define a cavity 544 between the side walls 542 and a bore 546 in each of the side walls 542. The cavity 544 communicates with the channel 540. The first jaw 530 includes a distal portion 548 that includes spaced arms 550. Each of the spaced arms 550 defines a concavity 552 that receives the bosses 28 on the second beam 14 of the ligation clip 10 to support the ligation clip 10 on the first jaw 530.

The second jaw 532 includes a first end portion 554 that includes spaced hubs 556. Each of the spaced hubs 556 supports a pivot member 556a that is received within one of the bores 546 of the first jaw 530 to pivotably couple the second jaw 532 to the first jaw 530. The second jaw 532 also includes an arm 558 that extends from the first portion 554 of the second jaw 532 to a second portion 560 of the second jaw 532. The second portion 560 includes a pair of spaced support members 562 that define concavities 564. The concavities 564 receive the bosses 20 of the ligation clip 10 to support the first beam 12 of the ligation clip 10 on the second jaw 532 (FIG. 21).

The actuator rod 534 is movable within the channel 540 of the rail 538 and the cavity 544 of the stationary jaw 530 between an advanced position (FIG. 21) and a retracted position (FIG. 25) and includes a distal portion 566 that has a forked member 568. The forked member 568 includes two tines 568a. Each of the tines 568a is coupled to one of the spaced hubs 556 of the second jaw 532 by a flexible coupling member 570. The connection point between the flexible coupling member 570 and the spaced hubs 556 is positioned outwardly of a transverse axis defined by the pivot members 556a of the second jaw 532. When the actuator rod 534 is moved from an advanced position (FIG. 21) to a retracted position (FIG. 25) within the channel 540 of the rail 538, the tines 568a cause the second jaw 532 to pivot about the transverse axis defined by the pivot member 556a to pivot the second jaw 532 in relation to the first jaw 530 from on open position (FIG. 21) to a clamped position (FIG. 25).

When the clip applier 500 (FIG. 19) is used by a clinician to position a ligation clip 10 onto tissue endoscopically, the elongate shaft 512 and the tool assembly 514 are inserted through a cannula and/or an incision in a patient's body to access the surgical site. When the tool assembly 514 is inserted through the cannula, the tool assembly 514 is in the open position. In the open position, the first jaw 530 is longitudinally aligned with the second jaw 532 to facilitate placement through a small diameter incision or cannula. As shown in FIG. 21, the ligation clip 10 is supported within the first and second jaws 530, 532 in the fully open position. In the fully open position, the beams 12, 14 are supported on the first and second jaws 530 and 532 and such that the clamping surface 22, 32 of the first and second beams 12, 14, respectively, of the ligation clip 10 are longitudinally aligned and face in substantially the same direction. The bosses 28 of the second beam 14 are received in the concavities 552 of the second jaw 14 and the bosses 20 received in the concavities 564 of the second jaw 53. In the open position, the width of the ligation clip 10 is minimized to facilitate receipt of the ligation clip 10 within a reduced diameter elongate shaft 512 and/or delivery of the ligation clip 10 through a small diameter cannula and/or incision. In addition, the ligation clip 10 is in a relaxed condition such that minimal strain is placed on the clip 10 prior to application of the clip 10 to tissue "T" (FIG. 25).

Figure 23:
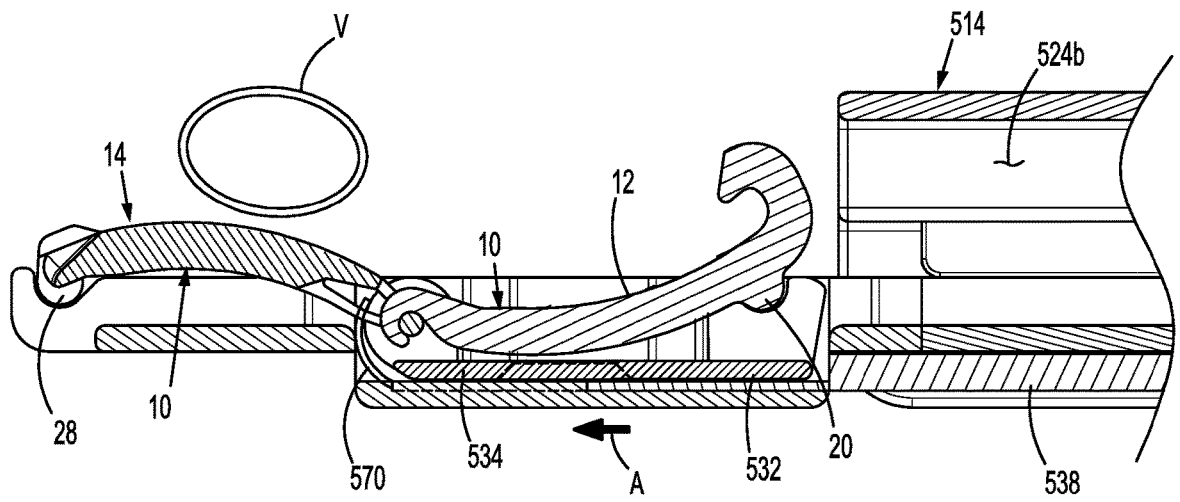
FIG. 23 is a cross-sectional view taken along section line 23-23 of FIG. 22.

FIGS. 22 and 23 illustrate the clip applier 500 with the tool assembly 514 moved to the advanced position extended from the elongate shaft 512. The tool assembly 514 is moved to the advanced position in the direction indicated by arrow "A" via operation of the trigger assembly 510. As the tool assembly 514 is moved from the elongate shaft 512, the first jaw 530 is moved through the distal end of the elongate shaft 512 to expose the ligation clip 10 in the open position.

Figure 24:
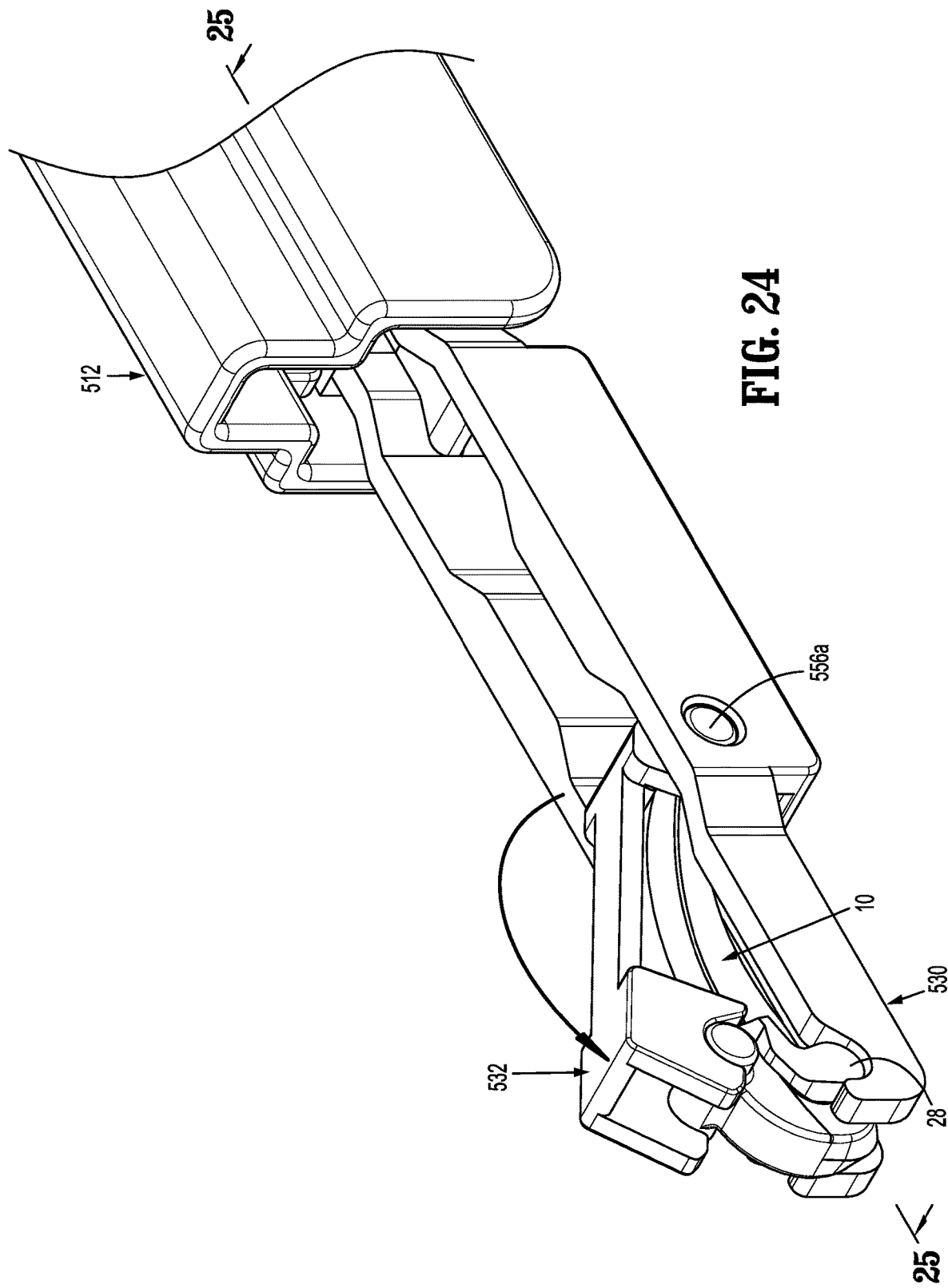
FIG. 24 is a side perspective view of the distal portion of the clip applier shown in FIG. 19 with the tool assembly in an advanced position as the tool assembly is moved from the open position towards the clamped position.
Figure 25:
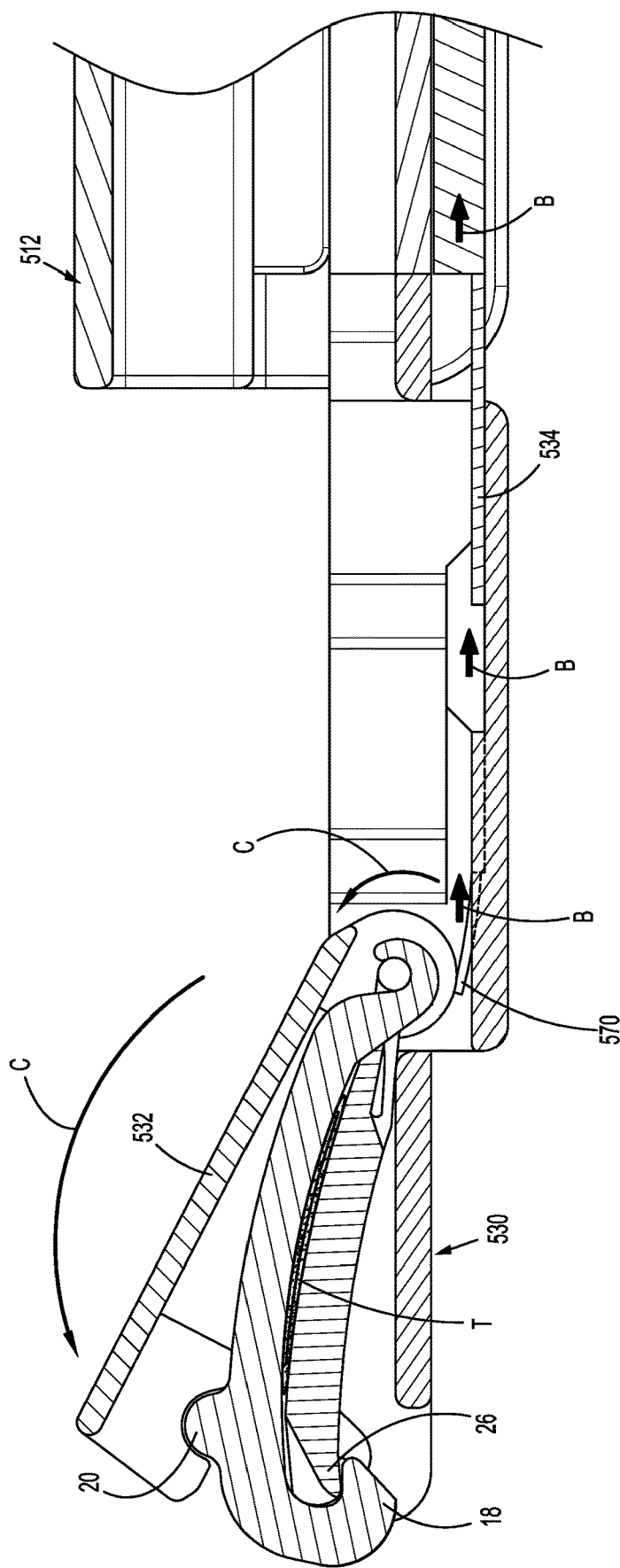
FIG. 25 is a cross-sectional view taken along section line 25-25 of FIG. 24.

FIGS. 24 and 25 illustrate the distal portion of the clip applier 500 (FIG. 19) as the tool assembly 514 is actuated to apply the ligation clip 10 about the tissue "T". When the tool assembly 514 is actuated to apply the ligation clip 10 about the tissue "T", the actuator rod 534 (FIG. 25) is moved from its advanced position to its retracted position in the direction indicated by arrows "B" in FIG. 25 to move the flexible coupling members 570 about the transverse pivot axis defined by the pivot members 556a to pivot the second jaw 532 in the direction indicated by arrows "C". As the second jaw 532 pivots towards the first jaw 530, the first beam 12 of the ligation clip 10 is pivoted towards the second beam 14 to move the first locking element 18 of the first beam 12 into latching engagement with the second locking element 26 of the second beam 14 to retain the ligation clip 10 in the clamped position.

Although not illustrated, the ligation clips 200, and 300 can be applied to tissue using the clip applier 500. In aspects of the disclosure, the ligation clips 200, 300 can be delivered to a surgical site with the first and second beams separated from each other, wherein the first and second beams 12, 14 are joined immediately prior to application of the ligation clip 10, 200, 300 to tissue. For example, the clip applier 500 may be provided to deliver clips 10, 200, 300 to jaws of the clip applier with the first and second beams separated from each other so that the width of the clip is minimized to facilitate receipt of the clip within a small diameter shaft and to minimize strain on the ligation clip or portions of the ligation clip. As discussed above, this prevents degradation of the condition and/or the performance of the ligation clip during storage of the clip within the clip applier and/or during delivery of the ligation clip to the surgical site.

Although not described in detail herein, it is envisioned that the exemplary aspects of the ligation clips described in this application can be formed from resilient polymeric materials including. Other materials of construction are also envisioned.

Persons skilled in the art will understand that the devices and methods specifically described herein and illustrated in the accompanying drawings are non-limiting exemplary aspects of the disclosed ligation clip. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosed ligation clip. Accordingly, the disclosure is not to be limited by what has been particularly shown and described, except as indicated by the appended claims.

What is claimed is:

1. A ligation clip comprising:
a first beam having a first end portion, a second end portion, and a first clamping surface positioned between the first end portion and the second end portion, the first end portion including a hook and the second end portion including a latch;
a second beam having a first end portion and a second end portion, the second beam including side walls and having an upper surface and a second clamping surface positioned between the first end portion and the second end portion, the first end portion of the second beam including a transverse post defining one side of a first through bore extending between the upper surface and the second clamping surface, the first end portion of the second beam defining a second through bore that extends between the side walls of the second beam, and the second end portion of the second beam defining a channel,
wherein the hook is configured to be inserted through the first through bore to releasably couple to the transverse post and pivotably secure the first beam to the second beam,
wherein the first beam is movable in relation to the second beam to move the ligation clip from an open position to a clamped position, the latch configured to engage the channel to secure the ligation clip in the clamped position, and
wherein the second through bore forms a flexible portion that is positioned to engage the first beam as the ligation clip is moved from the open position towards the clamped position to urge the ligation clip towards the open position.

2. The ligation clip of claim 1, wherein the hook defines a semi-cylindrical recess, and wherein the transverse post is received within the semi-cylindrical recess to pivotably couple the first beam to the second beam.

3. The ligation clip of claim 2, wherein the first beam includes first bosses positioned on each side of the second end portion of the first beam, and the second beam includes second bosses positioned on each side of the second end portion of the second beam.

4. A ligation clip comprising:
a first beam having a hook and defining a first clamping surface;
a second beam including sidewalls and having an upper surface and a second clamping surface, the second beam having a transverse post defining one side of a first through bore extending between the upper surface and the second clamping surface, the second beam defining a second through bore that extends between the side walls of the second beam,
wherein the hook of the first beam is configured to be inserted through the first through bore to releasably couple to the transverse post to pivotably secure the first beam to the second beam,
wherein when the first beam is coupled to the second beam, the ligation clip is movable between an open position and a clamped position,
wherein the second through bore forms a flexible portion that is positioned to engage the first beam as the ligation clip is moved from the open position towards the clamped position to urge the ligation clip towards the open position, and
wherein in the open position, the first beam is aligned with the second beam and the first clamping surface and the second clamping surface face in a common direction.

5. The ligation clip of claim 4, wherein the first beam and the second beam of the ligation clip are formed from a polymeric material.

6. The ligation clip of claim 4, wherein the hook and the transverse post are configured to cause minimal strain on the first beam and the second beam when the ligation clip is in the open position.

7. The ligation clip of claim 4, wherein the second beam has a first end portion and a second end portion, and wherein the second end portion of the second beam includes bosses that are adapted to support the ligation clip within a clip applier.

8. The ligation clip of claim 4, wherein the first beam has a first end portion and a second end portion, and wherein the second end portion of the first beam includes bosses positioned on each side of the second end portion.

9. A ligation clip comprising:
a first beam formed of a polymeric material, the first beam having a first end portion, a second end portion, and a first clamping surface positioned between the first end portion and the second end portion, the first end portion including a hook portion and the second end portion including a latch portion;
a second beam formed of a polymeric material, the second beam having a first end portion and a second end portion, the second beam having an upper surface and a second clamping surface positioned between the first end portion and the second end portion, the first end portion of the second beam including a transverse post defining one side of a first through bore extending between the upper surface and the second clamping surface, the first end of the second beam defining a second through bore that extends between side walls of the second beam, and the second end portion of the second beam defining a channel,
wherein the transverse post is configured to be received through the first through bore by the hook portion to releasably and pivotably couple the first beam to the second beam,
wherein when the first beam is coupled to the second beam, the first beam is pivotable in relation to the second beam to move the ligation clip from an open position to a clamped position, the latch configured to engage the channel to secure the ligation clip in the clamped position, and
wherein the second through bore forms a flexible portion in the first end of the second beam that is positioned to engage the first beam as the ligation clip is moved from the open position towards the clamped position to urge the ligation clip towards the open position.

10. The ligation clip of claim 9, wherein the hook portion defines a semi-cylindrical recess, and wherein the transverse post is releasably supported within the semi-cylindrical recess to pivotably couple the first beam to the second beam.

11. The ligation clip of claim 9, wherein the second end portion of the second beam includes bosses that are adapted to support the ligation clip within a clip applier.

12. The ligation clip of claim 9, wherein the first beam includes first bosses positioned on each side of the second end portion of the first beam, and the second beam includes second bosses positioned on each side of the second end portion of the second beam.

\* \* \* \* \*